(12) United States Patent
Hossainy

(10) Patent No.: US 6,709,514 B1
(45) Date of Patent: Mar. 23, 2004

(54) ROTARY COATING APPARATUS FOR COATING IMPLANTABLE MEDICAL DEVICES

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 10/040,574

(22) Filed: Dec. 28, 2001

(51) Int. Cl.⁷ .............................................. B05C 11/08
(52) U.S. Cl. ..................... 118/52; 118/56; 118/319; 118/320; 118/DIG. 16; 118/500
(58) Field of Search ............................ 118/52, 56, 319, 118/320, DIG. 16, 500; 239/223, 224; 427/240; 623/1.46, 1.47, 1.48

(56) References Cited

U.S. PATENT DOCUMENTS

| | | | |
|---|---|---|---|
| 3,288,052 A | 11/1966 | Hough | 99/235 |
| 4,148,932 A | 4/1979 | Tada et al. | 427/31 |
| 4,275,838 A | 6/1981 | Fangmeyer | 239/223 |
| 4,589,597 A | 5/1986 | Robisch et al. | 239/703 |
| 4,684,064 A | 8/1987 | Kwok | 239/223 |
| 4,795,095 A | 1/1989 | Shepard | 239/214.17 |
| 4,927,081 A | 5/1990 | Kwok et al. | 239/223 |
| 5,399,198 A * | 3/1995 | Ghaisas | 118/629 |
| 5,957,974 A * | 9/1999 | Thompson et al. | 623/1.13 |
| 6,045,864 A | 4/2000 | Lyons et al. | 427/255.23 |
| 6,189,804 B1 | 2/2001 | Vetter et al. | 239/7 |
| 6,267,073 B1 * | 7/2001 | Busse et al. | 118/24 |

* cited by examiner

*Primary Examiner*—Laura Edwards
(74) *Attorney, Agent, or Firm*—Squire, Sanders & Dempsey

(57) ABSTRACT

A rotary coating apparatus and a method of coating medical devices, such as stents, is disclosed.

17 Claims, 3 Drawing Sheets

ROTARY COATING APPARATUS FOR COATING IMPLANTABLE MEDICAL DEVICES

BACKGROUND OF THE INVENTION

1. Field of the Invention

This invention relates to an apparatus for coating medical devices, such as stents, and a method of using the same.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Vasospasms and recoil of the vessel wall also threaten vessel closure. Moreover, thrombosis and restenosis of the artery can develop over several months after the procedure, which can require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents can be used not only as a mechanical intervention but also as a vehicle for providing biological therapy. As a mechanical intervention, stents can act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Mechanical intervention via stents has reduced the rate of restenosis as compared to balloon angioplasty; restenosis, however, is still a significant clinical problem. When restenosis does occur in the stented segment, its treatment can be challenging, as clinical options are more limited as compared to lesions that were treated solely with a balloon.

Biological therapy can be achieved by medicating the stents. Medicated stents or therapeutic substance eluting stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

Although stents work well mechanically, the chronic issues of restenosis and, to a lesser extent, thrombosis remain. These events are adversely affected by the mechanical aspects of the stent such as the degree of injury and disturbance in hemodynamics caused by the stent. To the extent that the mechanical functionality of stents has been optimized, it has been postulated that continued improvements could be made by pharmacological therapies. Many systemic therapies have been tried. A challenge is maintaining the necessary concentration of a therapeutic substance at the lesion site for the necessary period of time. This can be done via brute force methods using oral or intravenous administration but the issues of systemic toxicity and side effects arise. Therefore, a preferred route can be achieved by local delivery of a therapeutic substance from the stent itself. Being made of metal, plain stents are not useful for therapeutic substance delivery. Therefore, a coating, usually made from a polymer, is applied to serve as a therapeutic substance reservoir. A solution of a polymer dissolved in a solvent and a therapeutic substance added thereto is applied to the stent and the solvent is allowed to evaporate. Accordingly, a polymeric coating impregnated with a therapeutic substance remains on the surface of the stent.

In order to be effectively applied with conventional spraying or dipping techniques, the solution needs to have a low viscosity. Low viscosities can be achieved by adding a higher fraction of solvent to the solution or by changing the composition of the solution with the addition of a wetting fluid. Compositions having a low viscosity require multiple applications of the composition and evaporation of the solvent in order to obtain a coating of suitable thickness, as compared to using compositions having greater viscosities. Accordingly, it is desired to use more viscous compositions to reduce the number of application steps and in effect reduce the processing time of forming the coating.

SUMMARY OF THE INVENTION

In accordance with one aspect of the embodiments of the invention, a method for coating stents is provided. The method can include applying a composition to a spinning disk member so the centripetal force that is applied to the composition by the disk member discharges the composition off of the disk member and onto the stent.

In one embodiment of the present invention, the method can include adjusting the temperature of the disk member to a temperature other than room temperature. The disk member can be flat, conical, or bowl-shaped. In one embodiment, the disk member can have a lip extending in an upwardly direction about the periphery thereof. The surface of the disk member can include grooves for altering the path of the composition.

In accordance with another aspect of the embodiments of the invention, an apparatus for coating a stent with a composition is provided. The apparatus includes a disk member capable of rotating about an axis of the disk member. The apparatus can also include a nozzle for applying the composition to the disk member and a motor for rotating the disk member.

DETAILED DESCRIPTION

Figure 1A:
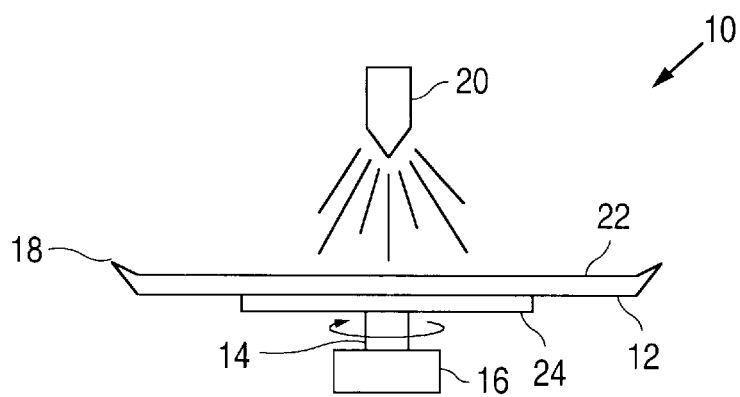
FIGS. 1A–1E illustrate various embodiments of the coating apparatus.
Figure 1B:
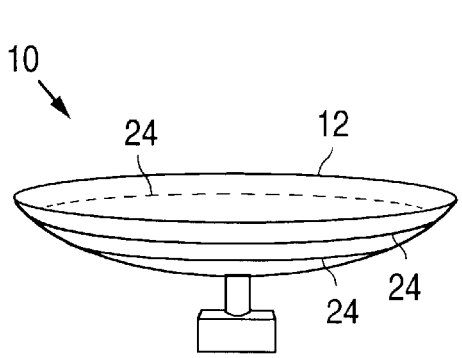
Figure 1C:
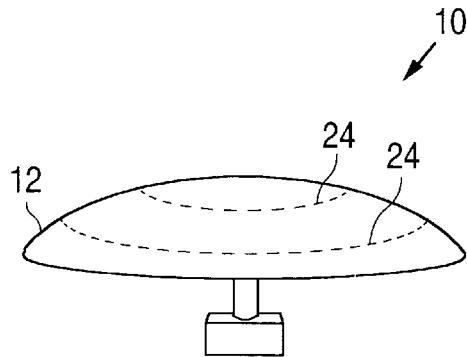
Figure 1D:
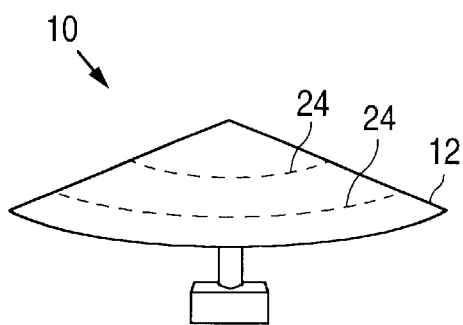
Figure 1E:
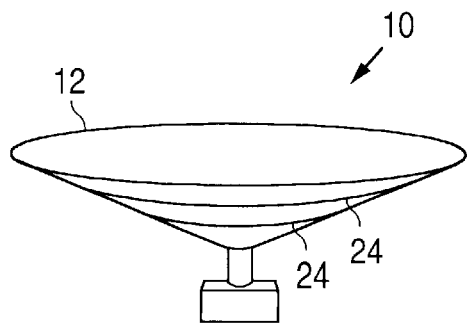

FIGS. 1A–1E illustrate embodiments of an apparatus 10 for coating medical devices, such as stents. Apparatus 10 can include a disk member 12 mounted on a shaft 14. The shaft 14, in turn, can be connected to a motor 16 for rotating the disk member 12 in a clockwise or counterclockwise direction. The disk member 12 can be flat (FIG. 1A), concave (FIG. 1B), convex (FIG. 1C) or conical (FIGS. 1D and 1E) in shape. The disk member 12 can optionally include a lip 18 disposed about the periphery thereof. The lip 18 can extend in an upwardly direction, towards a nozzle 20.

Figure 2A:
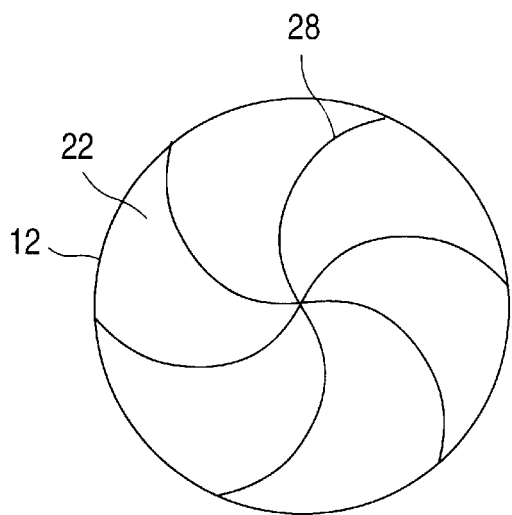
FIGS. 2A–2D illustrate disk members from various embodiments of the apparatus.
Figure 2B:
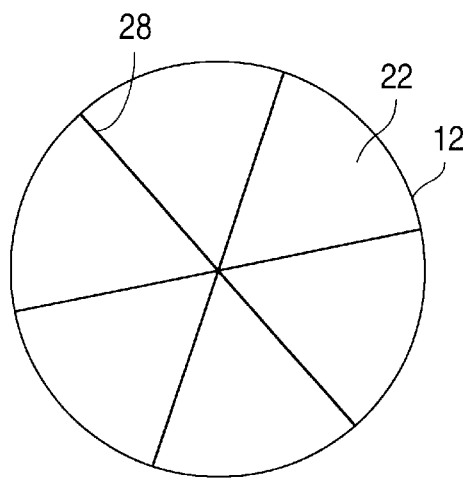
Figure 2C:
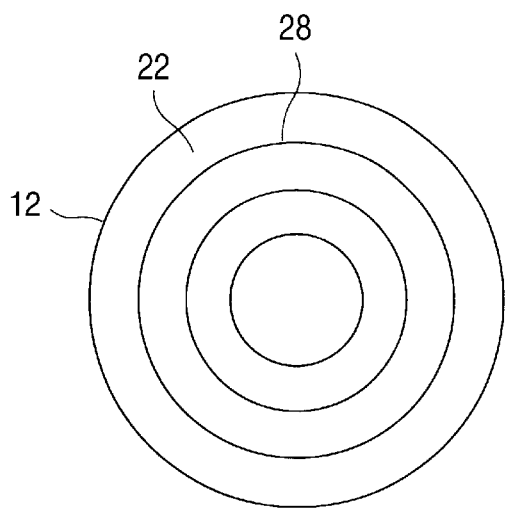
Figure 2D:
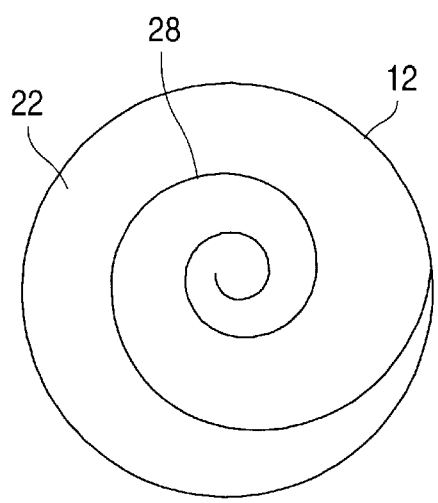

The disk member 12 can be made from any suitable material or can be coated with the desired material so as to minimize the ability of the composition to adhere to a surface 22 of the disk member 12 on which the composition is applied via the nozzle 20. One suitable non-stick surface 22 can be TEFLON. A temperature adjustor 24 can also be provided for adjusting the temperature of the composition during the coating process. The temperature adjustor 24 can be used to increase the temperature of the composition that includes a non-volatile solvent (e.g., dimethylsulfoxide (DMSO), dimethylformamide (DMF), and dimethylacetamide (DMAC)), or alternatively, can be used to decrease the temperature of the composition that includes a volatile solvent. A non-volatile solvent is a solvent that has a vapor pressure less than or equal to about 2.338 MPa (17.54 Torr) at ambient temperature. The diameter of the disk can range from about 5.1 cm (2.0 in.) to about 15 cm (6.0 in.), for example about 10 cm (4.0 in.). Referring to FIGS. 2A–2D, grooves or channels 28 can be carved within the surface 22 so as to provide control over the direction of the flow of the composition. FIG. 2A illustrates grooves 28 extending from the center of the disk member 12 to the outer edge of the disk member 12. FIG. 2B illustrates straight grooves 28. FIG. 2C illustrates circular grooves 28 positioned concentrically to one another. The depth and/or width of the grooves 28 can be incrementally smaller as the grooves 28 move closer to the edge of the disk member 12. Yet in another embodiment of the invention, groove 28 can be disposed in a spiral or corkscrew like fashion about the surface 22.

The apparatus 10 can be used for coating any suitable medical substrate that can be implanted in a human or veterinary patient. Examples of such implantable devices include balloon expandable stents, self-expandable stents, stent-grafts, grafts (e.g., aortic grafts), artificial heart valves, cerebrospinal fluid shunts, anastomosis devices, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), "MP35N," "MP20N," ELASTINITE (nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention.

The composition that can be applied by the nozzle 20 can include a polymeric material dissolved in a solvent. The polymeric material can also be emulsified in a solid concentration in a carrier such as water with about 10 weight percent to about 50 weight percent polymeric material. Optionally, a therapeutic substance can be added therein. Without a therapeutic substance added therein, the composition can be used to form a primer layer or a topcoat layer.

Representative examples of polymers that can be used include ethylene vinyl alcohol copolymer (commonly known by the generic name EVOH or by the trade name EVAL), poly(hydroxyvalerate); poly(L-lactic acid); polycaprolactone; poly(lactide-co-glycolide); poly (hydroxybutyrate); poly(hydroxybutyrate-co-valerate); polydioxanone; polyorthoester; polyanhydride; poly (glycolic acid); poly(D,L-lactic acid); poly(glycolic acid-co-trimethylene carbonate); polyphosphoester; polyphosphoester urethane; poly(amino acids); cyanoacrylates; poly (trimethylene carbonate); poly(iminocarbonate); copoly (ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

A solvent can be defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-1butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The therapeutic substance or active agent can be for inhibiting the activity of vascular smooth muscle cells. More specifically, the active agent can be aimed at inhibiting abnormal or inappropriate migration and/or proliferation of smooth muscle cells for the inhibition of restenosis. The active agent can also include any substance capable of exerting a therapeutic or prophylactic effect in the practice of the present invention. For example, the agent can be for enhancing wound healing in a vascular site or improving the structural and elastic properties of the vascular site. Examples of agents include antiproliferative substances such as actinomycin D, or derivatives and analogs thereof (manufactured by Sigma-Aldrich 1001 West Saint Paul Avenue, Milwaukee, Wisc. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, antiinflammatory, antiplatelet, anticoagulant, antifibrin, antithrombin, antimitotic, antibiotic, antiallergic and antioxidant substances. Examples of such antineoplastics and/or antimitotics include paclitaxel (e.g. TAXOL® by Bristol-Myers Squibb Co., Stamford, Conn.), docetaxel (e.g. Taxotere®, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax a (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® & and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which can be appropriate include alphainterferon, genetically engineered epithelial cells, rapamycin and dexamethasone.

Figure 3:
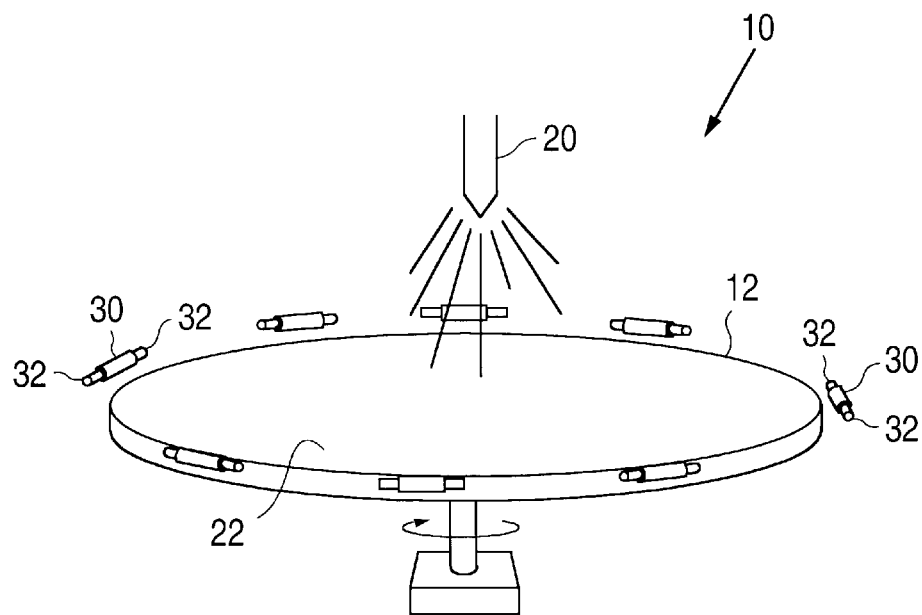
FIG. 3 illustrates an embodiment of the apparatus in use.
Figure 4A:
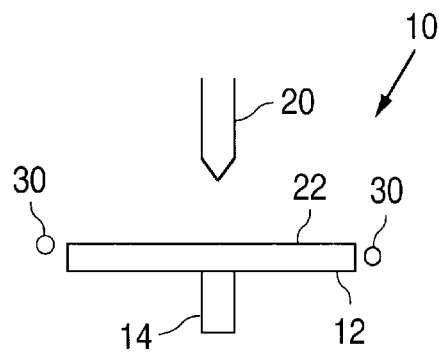
FIGS. 4a and 4b illustrate possible positions of implantable devices with respect to the apparatus.
Figure 4B:
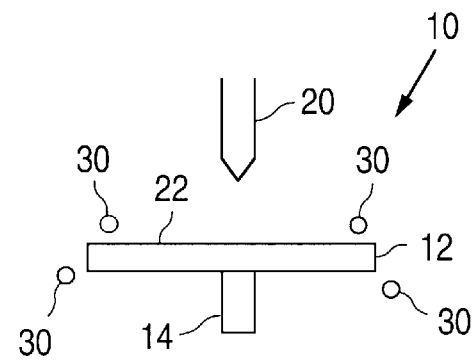

Referring to FIG. 3, a medical device, for example a stent 30, can be positioned in close proximity to the edge of the disk member 12, for example at a distance of about 0.5 mm (0.02 in.) to about 5.0 mm (0.20 in.). For disk member speeds between about 1,000 rpm and about 20,000 rpm, the stent 30 can be placed to the side of the disk member 12, with the longitudinal axis of the stent 30 above or slightly above the surface 22 of the disk member 12, as illustrated in FIG. 4a. For speeds below about 1,000 rpm, the stent 30 should be placed so that the longitudinal axis is below the surface 22, as illustrated in FIG. 4b. For coating stents, the stent 30 can be positioned on a mandrel 32 for rotating the stent 30 about the longitudinal axis of the stent 30. The composition can be applied to the disk member 12 while the disk member 12 is spinning at about 100 rpm to about 20,000 rpm. The flow rate of the solution from the nozzle 20 can be from about 1.0 g/min. (0.16 lbs./hour) to about 31 g/min. (5.0 lbs./hour). With the use of apparatus 10, the polymer content of the solution can be greater than about 80% of the solution, more narrowly greater than about 90%, for example greater than about 95%, without the increased viscosity affecting the coating process of the devices. The centripetal force applied to the solution causes the solution for flow off the disk member 12 and onto the stent 30. The temperature of the solution can be, for example, about 140° C. to about 240° C., more narrowly about 140° C. to about 200° C., yet more narrowly about 140° C. to about 190° C.

Although the invention has been disclosed in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An apparatus for coating a stent with a coating material, comprising a disk member having a surface that prevents or minimizes the ability of a coating material to adhere to the surface of the disk member, the disk member capable of rotating about an axis of the disk member, wherein a force caused by the rotation of the disk member causes the coating material applied to the surface of the disk member by a nozzle to discharge off of the disk member and onto a stent.

2. The apparatus of claim 1, further comprising a temperature controller for adjusting the temperature of the disk member to a temperature other than room temperature.

3. The apparatus of claim 1, wherein the surface of the disk member on which the coating material is applied includes at least one grove for altering the path of the coating material on the surface of the disk member.

4. The apparatus of claim 1, wherein the disk member is flat, conical or bowl-shaped.

5. The apparatus of claim 1, wherein the disk member comprises a lip extending in an upwardly direction about the periphery thereof.

6. The apparatus of claim 1, further comprising a motor for spinning the disk member.

7. The apparatus of claim 1, wherein the nozzle is positioned over a central region of the disk member.

8. The apparatus of claim 1, further comprising a stent holder for supporting the stent in close proximity to the disk member.

9. The apparatus of claim 1, further comprising a support assembly for supporting the stent in close proximity to the disk member and for rotating the stent about an axis of the stent.

10. The apparatus of claim 1, wherein the surface is made from polytetrafluoroethylene.

11. The apparatus of claim 3, wherein the at least one groove extends from the center of the disk member to an outer edge of the disk member.

12. The apparatus of claim 3, wherein the a least one groove is straight in form.

13. An apparatus for coating a stent with a coating material, comprising a disk member capable of rotating about an axis of the disk member, wherein a force caused by the rotation of the disk member causes the coating material applied to a surface of the disk member by a nozzle to discharge off of the disk member and onto stent, wherein the surface of the disk member on which the coating material is applied includes at least one groove for altering the path of the coating material on the surface of the disk member, the at least one groove being circular in form.

14. An apparatus for coating a stent with a coating material, comprising a disk member capable of rotating about an axis of the disk member, wherein a force caused by the rotation of the disk member causes the coating material applied to a surface of the disk member by a nozzle to discharge off of the disk member and onto a stent, wherein the surface of the disk member includes multiple grooves positioned concentrically to one another.

15. The apparatus of claim 14, wherein the depth of each groove is incrementally smaller as the grooves move closer to an edge of the disc member.

16. An apparatus for coating a stent with a coating material, comprising a disk member capable of rotating about an axis of the disk member, wherein a force caused by the rotation of the disk member causes the coating material applied to a surface of the disk member by a nozzle to discharge off of the disk member and onto a stent, wherein the surface of the disk member includes multiple grooves having a variable depths.

17. A apparatus for coating a stent with a coating material, comprising a disk member capable of rotating about an axis of the disk member, wherein a force caused by the rotation of the disk member causes the coating material applied to a surface of the disk member by a nozzle to discharge off of the disk member and onto a stent, wherein the surface of the disk member on which the coating material is applied includes a groove for altering the path of the coating material on the surface of the disk member, wherein the groove is spiral in form.

* * * * *